United States Patent [19]
Sakota et al.

[11] Patent Number: 5,178,831
[45] Date of Patent: Jan. 12, 1993

[54] DEVICE FOR TESTING BODY FLUIDS

[75] Inventors: Kazuyuki Sakota, Oi; Junichi Kondo, Musashino; Masanao Watanabe, Nerima, all of Japan

[73] Assignee: Dai Nippon Insatsu Kab Ushiki Kaisha

[21] Appl. No.: 746,190

[22] Filed: Aug. 15, 1991

Related U.S. Application Data

[63] Continuation of Ser. No. 231,837, Jun. 3, 1988, abandoned.

[30] Foreign Application Priority Data

Oct. 8, 1986 [JP] Japan ............... 61-239696
Jan. 27, 1987 [JP] Japan ............... 62-16432
Mar. 10, 1987 [JP] Japan ............... 62-55009

[51] Int. Cl.$^5$ ............... G01N 31/22; G01N 33/52
[52] U.S. Cl. ............... 422/56; 422/57; 422/58; 435/805; 435/970; 436/164; 436/169
[58] Field of Search ............... 422/55-58; 436/169, 170, 164; 435/805, 970

[56] References Cited

U.S. PATENT DOCUMENTS

| | | | |
|---|---|---|---|
| 2,785,958 | 3/1957 | Copenhefer et al. | 436/169 |
| 3,598,704 | 8/1971 | Dahlquist | 435/14 |
| 3,681,027 | 8/1972 | Smith | 436/169 |
| 3,891,507 | 6/1975 | Breuer | 436/169 |
| 4,126,417 | 11/1978 | Edwards | 422/56 |
| 4,258,001 | 3/1981 | Pierce et al. | 436/170 |
| 4,486,536 | 12/1984 | Baker et al. | 422/56 |
| 4,683,209 | 7/1987 | Ismail et al. | 436/14 |
| 4,797,256 | 1/1989 | Watlington, IV | 422/56 |

FOREIGN PATENT DOCUMENTS 2263469 11/1987 Japan ............... 435/14

Primary Examiner—Jill A. Johnston
Attorney, Agent, or Firm—Parkhurst, Wendel & Rossi

[57] ABSTRACT

A device for testing body fluids includes (a) a test reagent layer (1) formed on a substrate (5) and containing a test reagent, the tone of which changes according to the content of a test-objective material in a solution to be tested, and (b) a tone layer for criterion (3) formed on the substrate (5) and having a color formed by a dye or the like. The tone layer is used in order to judge the hue of the resulting color of the test reagent layer, wherein both the test layer (1) and the tone layer (3) have the property of absorbing the solution to be tested, and the hue of the resulting color of the test reagent layer and the hue of the tone layer can be compared by their wet colors, thereby affording a highly precise body fluid test.

14 Claims, 2 Drawing Sheets

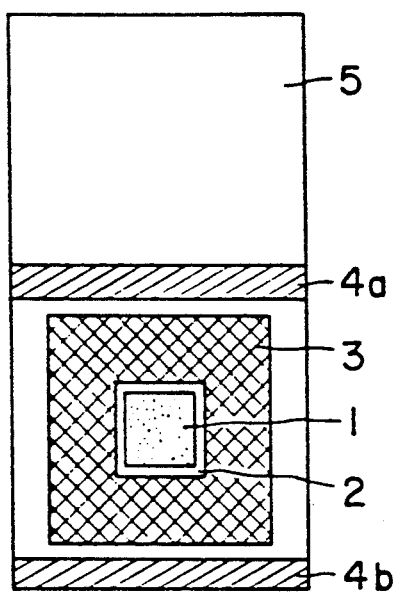
F I G. 1
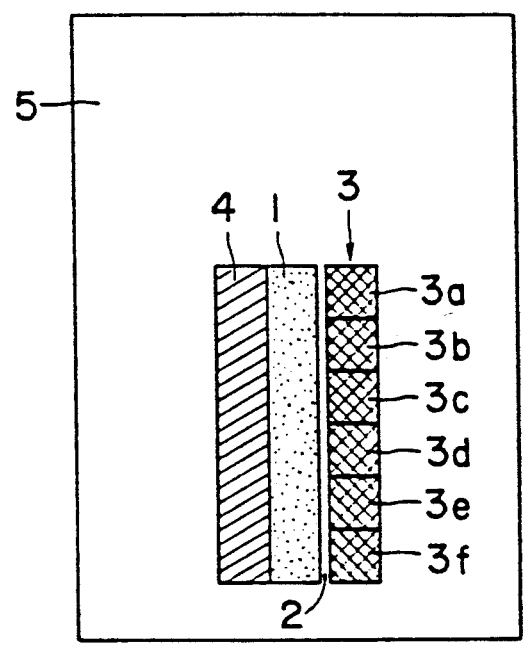
F I G. 2
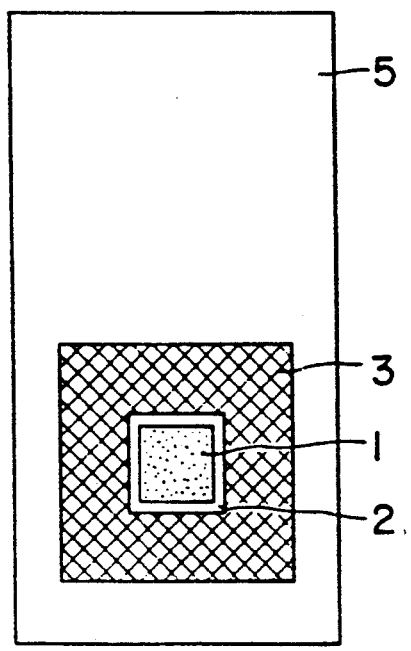
F I G. 3
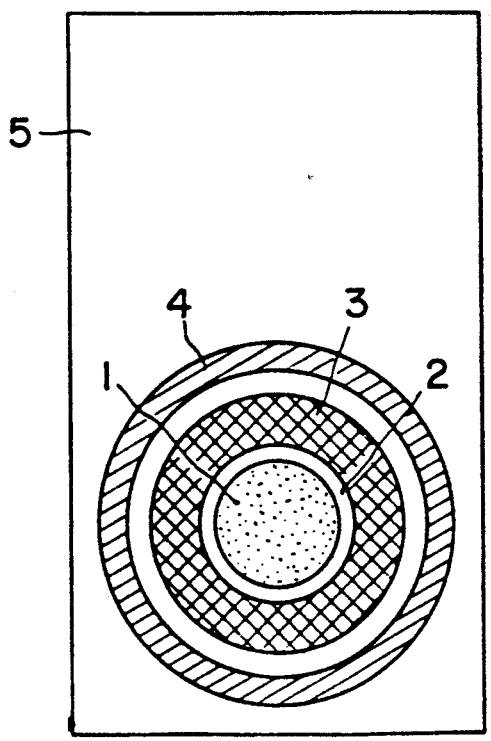
F I G. 4

DEVICE FOR TESTING BODY FLUIDS

This is a continuation application of Ser. No. 07/231,837, filed Jun. 3, 1988, now abandoned.

TECHNICAL FIELD

The present invention relates to a device for testing body fluids capable of simply detecting test-objective ingredients in body fluids and at the same time capable of carrying out judgment of the amount of the detected ingredients. More particularly the present invention relates to a device for testing body fluids capable of detecting glucose and protein in body fluids and the pH thereof, and at the same time capable of accurately and highly precisely judging the concentration of test-objective ingredients of solutions to be tested.

BACKGROUND ART

In the detection, diagnosis and treatment of diseases, it is highly important to simply and quickly detect the presence of certain ingredients contained in blood, lymph, urine and other body fluids while determining the amount thereof.

For example, quick and simple determination of the amount of glucose in a body fluid such as urine or blood is a prime desideratum to early detection, diagnosis and control of diabetes. Quick and simple determination of the amount of the protein in a body fluid, particularly urine, assumes an important role in the early detection, diagnosis and treatment of gastropathy. Accurate determination of the pH of a body fluid, particularly urine, can aid not only in detection of the presence of protein therein but also in confirmation of the possible bacteriuria which induces pyelitis, cystitis and like urosis.

As indicated above, it is of crucial importance to simply and quickly detect a variety of test-objective ingredients in a body fluid. For this purpose, a test device comprising a test reagent-impregnated filter paper affixed to a support has heretofore been used in most cases. Further, there have been attempts to develop test devices which can be obtained by a simplified process and is suitable for mass production. Such test devices have been produced by incorporating materials such as a polymeric binder and a water-absorptive carrier in a test reagent to prepare an ink composition suitable for printing or coating, applying the ink composition onto a support by printing (including coating), and drying the ink composition thus applied onto the support to form a test piece. The test reagent layer of the thus obtained test device for body fluids changes its tone depending upon the content of test-objective materials in a solution to be tested, and the content of the test-objective materials is detected by comparing a color formed by immersion in the solution to be tested with a tone table for criterion printed on a paper different from the test device.

On the other hand, when these test devices are immersed in a solution to be tested and thereafter the resulting color is compared with a separately provided tone table for criterion, the operations are cumbersome and the solution to be tested per se is colored. Accordingly, the change of the tone formed by the reaction of the test reagent with the test-purpose material in the solution to be tested is not accurately represented by the color of the test device; it is difficult to compare the color of the test device with the tone table for criterion; and an accurate test cannot be carried out in some cases.

Thus, in order to solve such problems, a test device wherein a substrate of the test device is provided with a test reagent layer containing a test reagent, and a tone layer for criterion which is provided by printing a printing ink composition in the vicinity of said test reagent layer has been proposed.

As described above, when the test device comprising the test reagent layer and the tone layer for criterion both formed on the substrate is immersed in a solution to be tested, and the color of the test reagent layer is compared with the tone layer for criterion, it is possible to avoid a judgment error due to color formation of the solution to be tested or the like.

However, as described in the prior art, when the tone layer for criterion is printed on the substrate using conventional ink compositions, the following drawbacks occur. While uniform color formation occurs at the surface of the test reagent layer, the solution to be tested merely deposits on the printed surface of the tone layer in the form of droplets due to differences in surface tension between the printed surface of the tone layer and the surface of the test reagent layer as well as differences in physical shape or state of their surfaces. Accordingly, the tone of the tone layer becomes uneven and it is difficult to compare the color of the tone layer with the color of the test reagent layer.

Further, in the prior art test device for body fluids, a considerable difference exists between the water-absorption properties of the reagent layer and the tone layer, and therefore comparison of hues cannot be carried out under equivalent conditions. This results in reduced test precision.

DISCLOSURE OF INVENTION

The present invention seeks to solve the problems of the prior art described above. An object of the present invention is to provide a device for testing body fluids wherein simple and accurate determination can be carried out.

In order to achieve the objects described above, a device for testing body fluids according to the present invention is characterized in that it comprises (a) a test reagent layer formed on a substrate and containing a test reagent tone which changes according to the content of a test-objective material in a solution to be tested, and (b) a tone layer for criterion formed on the substrate, which has a color formed by a dye or the like and is used in order to determine the hue of the resulting color of the test reagent layer. Further both the test reagent layer and the tone layer have the property of absorbing the solution to be tested, and the hue of the resulting color of the test reagent layer and the hue of the tone layer can be compared by their wet colors, i.e., colors in their wet state thereby affording a highly precise body fluid test.

BRIEF DESCRIPTION OF THE DRAWINGS

FIGS. 1 through 8 are plan views of respective examples of devices for testing body fluids according to the present invention.

BEST MODE FOR CARRYING OUT THE INVENTION

Figure 5:
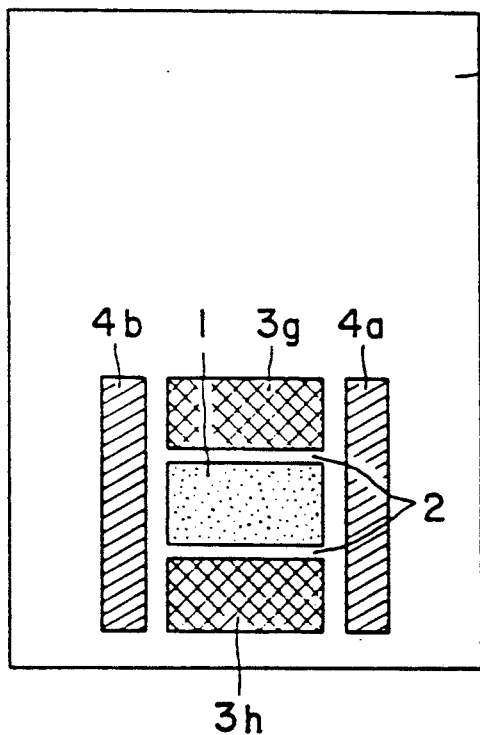

As shown in plan view in FIG. 1, an example of a device for testing body fluids according to the present invention comprises a sheet-like substrate 5 provided thereon with a test reagent layer 1 and a tone layer 3 for criterion provided so that it surrounds the periphery of the test reagent layer 1 via an intervening gap 2. In the test device for body fluids of the present invention, highly water-absorptive portions 4a and 4b may be provided at the periphery of the tone layer 3 described above so that they are spaced apart from the tone layer 3.

In the present invention, both the test reagent layer 1 and the tone layer for criterion 3 described above have the property of absorbing a solution to be tested and the states of "wetting" of both layers by the solution to be tested are rendered even. This permits accurate judgment of the content of a test-objective material in a solution to be tested.

With respect to the shape and arrangement of the above constitutional elements in the present invention, various modifications can be made. These modifications are described hereinafter.

Each constitutional element of the present invention will now be described in detail.

Substrate

Materials which have heretofore been used as substrates of devices for testing body fluids can be suitably used as the substrate. The substrates which can be used in the present invention are preferably those which do not react with a reagent composition and which do not prohibit color formation of a reagent layer described hereinafter. Examples of such substrates which can be used are papers, synthetic papers, nonwoven fabrics, synthetic resin films, and laminates of paper and a synthetic resin film.

Test Reagent Layer

A test reagent layer according to the present invention is one wherein capacity to absorb water is imparted to the test reagent layer by suitably adding a binder and a water-absorptive powder to a reagent composition selected according to the test purposes. When the test reagent composition per se has suitable capacity to absorb water or when a test reagent layer is produced by impregnating a filter paper with a test reagent composition, the water-absorptive powder is not necessarily added.

When a filter paper is used, fibers stand at the surface of the filter paper. Accordingly, a solution to be tested is liable to show stagnation and remains at the surface without absorbing a portion of the solution to be tested.

Japanese Patent Pub. No. 25953/1969 discloses a process for providing a test reagent layer on a substrate by previously dissolving enzymes in a water-alcohol mixture, incorporating an indicator, a pH buffer, a polymeric binder and a water-absorptive carrier in the resulting solution to prepare an ink composition suitable for printing or coating, applying the ink composition onto a substrate by printing (including coating), and thereafter drying the ink composition.

More preferably, a test reagent layer can be formed by using at least one of an ink composition for glucose detection, an ink composition for protein detection or an ink composition for the pH determination as described in Japanese Patent Application No. 107871/1986 previously filed by us.

Such ink compositions are as follows:

(a) An ink composition for detecting glucose which comprises a reagent composition comprising a saccharide-oxidizing enzyme, peroxidase, an oxidizable indicator, a wetting agent, a sensitivity modifier, a stabilizer, a pH buffer, a binder and a water-absorptive powder, dissolved or dispersed in a nonaqueous solvent.

(b) An ink composition for detecting protein which comprises a reagent composition comprising an indicator which indicates a protein error, a pH buffer, a wetting agent, a protein-adsorptive ion exchanger, a form-retaining agent, a binder and a water-absorptive powder, dissolved or dispersed in a solvent.

(c) An ink composition for the pH determination which comprises a reagent composition comprising a pH indicator, a quaternary ammonium salt or an amine salt, a basic material, a binder, and a water-absorptive powder, dissolved or dispersed in a solvent.

Test reagent principal ingredients of the ink compositions mentioned above will be described in greater detail.

(a) Ink composition for glucose detection

Glucose in a body fluid reacts with oxygen in the air by the action of a glucose-oxidizing enzyme such as glucose oxidase to be finally oxidized into gluconic acid and hydrogen peroxide. The hydrogen peroxide thus produced generates nascent oxygen by the action of peroxidase, which oxygen reacts immediately with an oxidizable indicator such as guaiacum resin or o-tolidine to cause the indicator to form color. The presence and amount of glucose in a body fluid are semiquantitatively determined by the degree of the color formation. Further, quantitative determination of the test device for glucose detection, i.e., a linearity between the concentration of glucose contained in a specimen and the color density of a test reagent portion can be improved by using an aliphatic carboxylic ester of ascorbic acid as the sensitivity modifier.

The stabilizer is one which prevents the discoloration of an oxidizable indicator due to the action of materials such as peroxides in an atmospheric air. While ascorbic acid and its fatty acid esters can be used as the stabilizer, other known compounds having antioxidant activity, or specific surfactants represented by glycerol esters or mixture thereof can also be suitably added. The pH buffer is one added so that the oxidizable indicator described above is kept at a pH at which it causes preferred color change in the ink composition for glucose detection. For example, a combination of citric acid with sodium citrate or the like is used.

These ingredients are dissolved or dispersed in a non-aqueous solvent containing substantially no water selected from aromatic hydrocarbons, aliphatic ketones, esters and alcohols excluding lower alcohols, together with a binder and a water-absorptive powder described hereinafter.

(b) Ink composition for protein detection

An ink composition for protein detection contains, as the form-retaining agent, a water-swelling resin having a carboxyl group as a functional group.

When an indicator which is maintained in the acidic pH range and indicates a protein error is caused to contact with protein in a body fluid to be tested, the indicator and protein form a complex, turning from the acidic color yellow to the basic color blue. The degree of this color change depends upon the amount of protein present in the body fluid to be tested. The presence of protein in the body fluid to be tested is detected on the basis of this mechanism.

The indicator which indicates a protein error behaves in accordance with the above described mechanism. Specific examples of the indicators are: Tetrabromophenol Blue, Tetrabromothymol Blue, ethyl esters of tetrabromophenolphthalein, tetrabromobenzalaniline, and Bromothymol Blue. Among these indicators, Tetrabromophenol Blue is preferred from the point of view of sensitivity.

The pH buffer is any buffer that can give the reagent composition a predetermined pH value. A combination of citric acid and sodium citrate is preferably used. Protein-adsorptive ion exchangers are strongly acidic cation exchangers (functional group:—$SO_3M$), weakly acidic cation exchangers (—COOM), strongly basic ion exchangers (—$N^+R$, $X^-$, —$N^+(CH_3)_2(CH_2CH_2O)$), weakly basic anion exchangers (—$N(R)_2$, —NH(R), —$NH_2$ and the like) and the like. The base materials of the ion exchangers mentioned above are synthetic resins such as styrene resins and acrylic resins, cellulose and silica.

A material which does not impair the hydrophilicity of the printed test reagent portion and which is water-insoluble is used as the form-retaining agent. Examples of such form-retaining agents are water-swelling resins having a carboxyl group as a functional group and known as a disintegrating agent for medicines such as calcium carboxymethyl cellulose and sodium carboxymethyl cellulose, and highly water-absorptive gels.

It is preferable that the reagents described above, a binder and a water-absorptive powder be dissolved or dispersed in a nonaqueous solvent selected from aromatic hydrocarbons, aliphatic hydrocarbons, esters and alcohols, or water or a mixture thereof to prepare an ink composition.

(c) Ink composition for pH determination

The pH of a body fluid is determined by judging the tones of the indicators which vary with the pH value.

Any pH indicator can be used provided that it is an indicator of the tone of which varies depending upon the hydrogen ion concentration of the solution to be tested. A plurality of indicators can also be suitably selected or used in combination to determine the pH of wide regions.

The incorporation of an appropriate amount of a quaternary ammonium salt in an ink composition inhibits greatly the fading phenomenon of a color which has once been formed and provides a distinct color. When a basic material is added, the elution of an acidic material after ink preparation can be prevented, thereby preventing the tone of an ink composition from changing with the elapse of time.

The reagents described above are uniformly dissolved or dispersed in a nonaqueous solvent selected from aromatic hydrocarbons, aliphatic hydrocarbons, esters and alcohols, or water or a mixture thereof, together with a binder and a water-absorptive powder.

Materials for the test reagent layer other than the test reagent principal ingredients described above, i.e., a binder and a water-absorptive powder will be described. Other materials can be added to the test reagent layer and the tone layer for criterion provided that they do not cause any tone change by ingredients contained in the solution to be tested. Further, the ingredients described above can be also added to the tone layer provided that they do not cause any tone change by the ingredients contained in the solution to be tested.

Binder

The binder should not affect the ingredients or pH of a solution to be tested, or the reagents, particularly the enzyme and the oxidizable indicator, nor prevent the color formation reaction.

Examples of binders which have been confirmed to meet such requirements are: (I) synthetic resins such as polyester resins, alkyd resins, polyurethane, polystyrene resins, acryl resins, epoxy resins, vinyl chloride resins, vinyl chloride copolymer resins, hydrophilic resins, e.g., polyvinyl butyral resins, polyvinyl alcohol resins or polyvinyl pyrrolidone resins, and maleic anhydride copolymers; (II) cellulose derivatives such as methyl cellulose, ethyl cellulose, hydroxyethyl cellulose, and carboxymethyl cellulose; and (III) natural polymers such as starch, polysaccharides, gelatin, casein, and sodium alginate. These binders may be used in combination.

Water-absorptive powder

The water-absorptive powder, when incorporated in the reagent composition, enhances the water absorption property of the reagent composition formed on the substrate, promotes the contact between the solution to be tested and the reagent composition, and also promotes the color formation reaction of the indicator.

A powder which shows extreme acidity or alkalinity when it comes into contact with water is unsuitable for use as the water-absorptive powder, while a powder having a high degree of white is preferred. Specific examples of the water-absorptive powder are: kaolin, synthetic silica, glass, cellulose block, microcrystalline cellulose, ion exchange cellulose, ion exchange resins, calcium carbonate, magnesium carbonate, and aluminum silicate.

It is desirable that the binder be used in an amount of from 3 parts by weight to 30 parts by weight, more preferably from 5 parts by weight to 20 parts by weight per 100 parts by weight of the water-absorptive powder from the standpoints of film-forming capacity and the property of absorbing the solution to be tested. If the amount of the binder is less than 3 parts by weight, its ability to bond will be insufficient, and the test device will disintegrate when a solution to be tested is absorbed. If the amount of the binder is more than 30 parts by weight, the property of absorbing the solution to be tested will be reduced and the color formation property will be impaired.

Wetting agent

In addition to the binder and the water-absorptive agent, the wetting agent can be optionally incorporated in the ink composition. Examples of the wetting agents include nonionic surfactants, anionic surfactants, cationic surfactants, amphoteric surfactants, and polyethylene glycols. The wetting agent serves to disperse each reagent, thus promoting the formation of a homogeneous reagent layer, and can improve wettability.

In addition to the embodiments described above, the test reagent layer according to the present invention can be prepared from a composition for occult blood detection or a composition for urobilinogen detection.

(d) Composition for occult blood detection

This composition for occult blood detection is characterized in that an organic hydroperoxide, an oxidizable indicator, a sensitizer, a pH buffer, a binder, and a water-absorptive powder are dissolved or dispersed in a nonaqueous solvent. The organic hydroperoxide alone, or a mixture of the organic hydroperoxide and the sensitizer is present in the same microcapsule.

According to the embodiment described above, the organic hydroperoxide alone or the mixture of the organic hydroperoxide and the sensitizer is enmicrocapsulated and the resulting microcapsule is used. Accordingly, the organic hydroperoxide does not react with other materials during storage. Since the sensitizer is used, the sensitivity of the reaction is high after microcapsule disintegration.

Ingredients of the composition for occult blood detection will be described.

Organic Hydroperoxide

Any of many well-known compounds belonging to the group can be used as the organic hydroperoxide so long as they exhibit detectable response such as change of light absorbed or reflected by the test device or color change obtained by reacting the organic hydroperoxide with a peroxide activator in the presence of an indicator having a sensitivity to the peroxide. Examples of such organic hydroperoxides are as follows:

cumene hydroperoxide, t-butyl hydroperoxide, 2,5-dimethylhexane-2,5-dihydroperoxide, diisopropylbenzene hydroperoxide, paramenthane hydroperoxide alone or mixtures thereof.

Of these, cumene hydroperoxide is preferably used.

The organic hydroperoxide can be present in an amount of from 1 to 30% by weight, preferably from 2 to 25% by weight of the solid content of the composition for occult blood detection.

Microcapsule film material

The microcapsule film material used in the composition described above is an emulsifier which prepares a good emulsion by mixing it with the organic hydroperoxide. It is desirable that the microcapsule film material be quickly disintegrated when it comes into contact with water in the solution to be tested and it serves to participate the self-contained organic hydroperoxide in the color formation reaction of the occult blood with the indicator.

Examples of the microcapsule film materials which have been confirmed to meet such requirements are as follows:

(i) Water-soluble synthetic resin

Polyvinyl alcohol resins, polyvinyl pyrrolidone resins, polyacrylamide resins, polyvinyl acetate resins and the like.

(ii) Water-soluble cellulose derivative

Methyl cellulose, ethyl cellulose, hydroxyethyl cellulose, carboxymethyl cellulose and the like.

(iii) Natural polymers and the like

Starch, polysaccharides, gelatin, casein, gum arabic, sodium alginate and the like.

Of these, gum arabic, carboxymethyl cellulose and polyvinyl alcohol resins are particularly preferred.

It is preferable that the microcapsule film material be present in an amount of from 2 to 70% by weight, preferably from 4 to 50% by weight of the solid content of the composition for occult blood detection.

Oxidizable indicator

The oxidizable indicator forms color by oxidation by oxygen, and known compounds such as benzidines and N-alkylated benzidines can be widely used. Of these, o-tolidine, 3,3',5,5'-tetramethylbenzidine, 2,7-azafluorene and the like are preferred, and 3,3',5,5'-tetramethylbenzidine is particularly preferred.

It is desirable that the oxidizable indicator be present in an amount of from 0.5 to 10% by weight, preferably form 0.6 to 6% by weight of the solid content of the composition for occult blood detection.

Sensitizer

The use of a mixture of quinoline or a derivative thereof and a triethanolamine salt as the sensitizer in the composition described above can promote the color formation of the test device for occult blood detection in the presence of blood to improve the sensitivity and color density.

Examples of quinoline and its derivatives for use herein include quinoline, quinine, 6-methoxyquinoline, 6-methylquinoline, and 7-methylquinoline. Of these, 6-methoxyquinoline is particularly preferred.

Examples of triethanolamine salts for use herein include triethanolamine hydrochlorides, triethanolamine phosphates, and triethanolamine sulfates. Of these, triethanolamine lauryl sulfate and triethanolamine polyoxylauryl sulfate which are sulfates are preferred, and triethanolamine lauryl sulfate is particularly preferred.

It is desirable that quinoline or its derivatives be present in an amount of from 0.5 to 10% by weight, preferably from 0.6 to 6% by weight of the solid content of the composition for occult blood detection.

It is desirable that the triethanolamine salt be present in an amount of from 1 to 20% by weight, preferably from 2 to 15% by weight of the solid content of the composition for occult blood detection.

Buffer

The pH buffer is used in order to keep the pH at a pH value in the vicinity of a pH at which the oxidizable indicator described above causes the preferred color change in the composition for occult blood detection. Any pH buffer can be used provided that it can impart a specific pH (e.g., a pH of 5) to the composition for occult blood detection. It is desirable that a combination of citric acid and sodium citrate be used.

The foregoing can be used as the binder. It is desirable that the binder be used in an amount of from 0.1 to 20% by weight, preferably from 0.5 to 10% by weight of the solid content of the composition for occult blood detection.

The foregoing can be used with the water-absorptive powder. It is desirable that the water-absorptive powder be used in an amount of from 30 to 90% by weight of the solid content of the composition for occult blood detection.

Solvent

The solvent similar to one used in the ink composition for glucose detection can be used.

Further, a background colorant such as oil yellow may also be added to make the tone of the color formed by the indicator more easily distinguishable.

(e) Composition for urobilinogen detection

This composition for detection is characterized in that an Ehrlich's reagent, a strongly acidic buffer, a binder, a water-absorptive powder and a reaction activator are dissolved or dispersed in a nonaqueous solvent.

According to the composition described above, a cationic surfactant inhibits the Ehrlich's reaction, whereas an anionic surfactant promotes the reaction of a test device and urobilinogen. A nonionic surfactant having an HLB within the range of from 6.0 to 11.0 improves the contact of the test device with urobilinogen.

Respective ingredients of the above composition for urobilinogen detection will be described.

Mechanism

When a p-di(alkyl)-aminobenzaldehyde which is an indicator comes into contact with urobilinogen under acidic conditions, a complex is formed. The resulting color exhibits from yellowish pink to reddish purple depending upon the concentration of urobilinogen present in a solution to be tested. This mechanism permits the detection of urobilinogen in the solution to be tested.

Ehrlich's reagent (indicator)

Specific examples of the Ehrlich's reagents are p-di(-lower alkyl)-aminobenzaldehydes such as p-dimethylaminobenzaldehyde and p-diethylaminobenzaldehyde. Of these, p-ethylaminobenzaldehyde is excellent from the standpoint of its sensitivity.

The Ehrlich's reagent is preferably used in the composition for detection in an amount of from 0.01 to 5% by weight.

Strongly acidic buffer

Since the reaction between urobilinogen and the indicator proceeds in the acidic region, an acid which can adjust the pH to no more than 3 and preferably which is a solid at room temperature is used for the purpose of imparting such reaction environment and for the purpose of inhibiting a side reaction. Specifically sulfosalicyclic acid, oxalic acid, p-toluene sulfonic acid, metaphosphoric acid and the like are used alone or in mixture.

The strongly acidic buffer is preferably used in the composition for detection in an amount of from 2 to 30% by weight.

Binder

The binder similar to one described above can be used. It is desirable that the binder be preferably used in the composition for detection in an amount of from 0.2 to 20% by weight.

Water-absorptive powder

The foregoing can be used as the water-absorptive powder. It is preferably that the water-absorptive powder be preferably used in the composition for detection in an amount of from 15 to 50% by weight.

Solvent

The foregoing can be used as the solvent. The solvent is preferably used in the composition for detection in an amount of from 30 to 85% by weight.

Reaction activator

An anionic surfactant or a nonionic surfactant is used as the reaction activator. Desirably, the anionic surfactant is used in combination with the nonionic surfactant.

Examples of the anionic surfactants include sodium lauryl sulfate and sodium dodecyl sulfonate. The anionic surfactant is preferably used in the composition for detection in an amount of from 0.05 to 3% by weight.

The nonionic surfactants are used alone or in mixture so that the HLB is within the range of from 6.0 to 11.0. Specific examples of the nonionic surfactants for use herein include polyoxyethylene ethers, fatty acid esters of sorbitan, esters of macrogol and fatty acids, and ethers of macrogol and alcohols. The nonionic surfactant is preferably used in the composition for detection in an amount of from 0.05 to 5% by weight.

Other ingredients

In addition to the principal ingredients described above, many auxiliary ingredients can be incorporated in the composition for urobilinogen detection. For example, the addition of caffeine can enhance the sensitivity of color formation. Further, an antioxidant and a chelating agent can be used as ingredients technically recognized. Furthermore, a background colorant may be added for the purpose of making the tone of the color formed by the indicator easily distinguishable.

Preparation of each composition for detection

Ingredients of each composition for detection are first pulverized so that the water-absorptive powder becomes particles having a diameter of no more than 50 μm. The resulting particles may be added to a solution or dispersion having other ingredients previously dissolved or dispersed in a solvent, and may be dispersed and mixed by means of a high speed stirrer, sand mill, ball mill, three-rod mill, supersonic disperser or the like.

Formation of test reagent layer

Each composition for detection is used as an ink composition and applied onto a support. Thereafter, the ink composition applied onto the support is dried to form each region for detection. Thus, a test device is obtained.

Application techniques suitable for use herein are printing processes, and coating processes (such as roll coating, spray coating, dip coating, solid coating).

In the embodiments described above, it is preferable that the amount of each composition for detection applied be relatively large and that the amount be constant, and therefore each composition for detection is preferably applied onto the substrate by the silk screen printing process, intaglio printing process, gravure printing process or the like.

While the amount of each composition for detection applied onto the substrate may vary depending upon the type of the composition, in general, the quantity is from 2 to 150 grams per square meter (on a dry basis).

Tone layer

The tone layer for criterion according to the present invention has a property of absorbing the solution to be tested and the hue of the formed color of the test reagent layer and the hue of the tone layer can be compared by their wet colors (in other words, in a wet state). Therefore, the constitutional ingredients of the tone layer are substantially the same as the ingredients other than the principal ingredients of the test reagent layer described above (i.e., active ingredients as the indicators).

Accordingly, an ink composition for tone layer is obtained by dissolving or dispersing the materials for the test reagent layer other than the test reagent principal ingredients described above in the same solvent as used in the ink composition, and imparting a color to the solution or dispersion by a dye such as a water-soluble dye or a pigment so that there are obtained tones which are consistent with colors at each concentration when a test reagent layer is immersed in a solution to be tested which has a normality.

A binder and a water-absorptive powder similar to those used in the test reagent layer described above can be used as the binder and the water-absorptive powder added as ingredients of the tone layer. The tone layers can be formed by applying the ink compositions for forming the tone layers, respectively.

Processes similar to those used in forming the test reagent layer as application techniques can be used. While the amount of the ink composition applied can vary depending upon the type of the ink composition, it is desirable that the amount be generally from 2 to 150 grams per square meter (on a dry basis).

Adjustment of water absorption capacity

In the present invention it is indispensable that both the test reagent layer and the tone layer have a property of absorbing a solution to be tested.

When the prior art test piece having no tone layer is used, the test piece is immersed in urine in a cup for sampling urine, and the end surface of the test piece is brought into contact with the upper edge of the cup for sampling urine to slide it, thereby removing excess urine.

However, when the present test piece having the tone layer is used, the removal manner as described above is not satisfactory. Particularly, when the tone layer surrounds the test reagent layer, only excess urine on the tone layer can be removed, and excess urine on the reagent layer cannot be thoroughly removed. Accordingly, it is necessary that both the reagent layer and the tone layer have a suitable absorption property. It is desirable that excess urine on the test reagent layer is absorbed by the tone layer when the test piece immersed in the cup for sampling is picked up. If the tone layer has a too large absorption property, it will suck up urine on the test reagent layer as well. Accordingly, the suitable absorption property is provided to the tone layer by adjusting the thickness, width and composition of the tone layer, and the intervals between the tone layer and the reagent layer. It is preferable that the water absorption property of the test reagent layer is approximate to the water absorption property of the tone layer. When the difference in water absorption property of both layers is within a certain limit, color formation and judgment can be carried out without any hindrance.

If the difference in water absorption property of both layers is too large, the following problems will occur.

(1) Water absorption property of the tone layer < water absorption property of the test reagent layer For example, a test device is immersed in urine and picked up. While the color formation reaction proceeds, urine between both layers and the tone layer transfer to the test reagent layer after color formation. This further induces the color formation reaction in the test reagent layer. As a result, the color density at the periphery of the test reagent layer is increased.

(2) Water absorption property of the tone layer > water absorption property of the test reagent layer In this case, a tendency that a body fluid, e.g., urine, transfers to the tone layer is increased, and therefore this remarkably promotes drying of the test reagent layer which has once formed a color. Its color changes to the hue different from the hue of the color in a wet state, and therefore an error is liable to occur in comparison of both layers.

While the present test devices for body fluids as described above can vary depending upon the type of the test reagent, it takes about 20 seconds until the color formation reaction proceeds after said test device has been immersed in the solution to be tested and picked up. Judgment is carried out by visual observation in 40 seconds after the color formation reaction is completed.

In a preferred embodiment of the present invention, it is preferable that the water absorption property of the test reagent layer be approximate to that of the tone layer. Considering the circumstances described above, it is desirable that the water absorption property of the tone be not extremely small as compared with that of the test reagent layer.

When the property of the tone layer for criterion and the test reagent layer of absorbing the solution to be tested is large, it is such an extent that the solution to be tested which is present at the surface of the test reagent layer or the tone layer penetrates into the inner portion of the layers immediately after the test device has been immersed in the solution to be tested and picked up. In the case of small absorption property, this absorption property is such an extent that the droplets of the solution to be tested remain at the surface of the layers for a period of the order of 20 seconds after the test device has been picked up.

In order to provide preferred and approximate properties of the test reagent layer and the tone layer of absorbing the solution to be tested, the absorption amount (weight) of each layer capable of absorbing the solution to be tested is preferably from 50 to 500%, more preferably from 100 to 300% of the dry weight of each layer. When the absorption amount is within this range, a test is carried out without any hindrance even if the absorption amounts of both layers are different.

Such an absorption amount is achieved by using the water-absorptive powder and the binder in each layer in a weight ratio of the water-absorptive powder to the binder of from 100:3 to 100:30, more preferably from 100:5 to 100:20 as described above.

In order to control the extent of the water absorption property, the following methods can be used alone or in combination with respect to the wetting agents, pH buffers, binders and fillers which are ingredients contained in the test reagent layer described above, which are materials of the test reagent layer other than the test reagent principal ingredient, and which is also used as materials of the tone layer:

(1) When the surfactant is used as the wetting agent, the surfactant is added to only the test reagent layer. Alternatively, the content of the surfactant in the test reagent layer is rendered larger or smaller than the content of the surfactant in the tone layer.

(2) The water-absorptive powder is used as the pH buffer and the pH buffer is added to only the test reagent layer. Alternatively, the content of the pH buffer in the test reagent layer is rendered larger or smaller than the content of the pH buffer in the tone layer.

(3) Resins having a different water absorption property are used as the binders, a resin having a high water absorption property is incorporated in the ingredients of the test reagent layer, and a resin having a low water absorption property is incorporated in the ingredients of the tone layer, or vice versa.

(4) The amount of the water-absorptive powder incorporated in the test reagent layer is rendered larger or smaller than that incorporated in the tone layer.

As stated hereinabove, the use of the tone layer having a composition approximate to that of the test reagent layer facilitates that they have an analogous property of absorbing the solution to be tested. However, it is possible to prepare a tone layer for protein detection based on the composition of test reagent layer other than the test reagent layer for protein detection, e.g., a tone layer for protein detection based on the composition of a test reagent layer for glucose detection in place of the employment of a tone layer for protein detection having a composition analogous to that of the test reagent layer for protein detection from the standpoint of only the water absorption property. In this case, it is necessary to confirm that the ingredients in the test reagent layer for glucose detection do not affect the test reagent layer for protein detection.

Highly water-absorptive portion

When excess solution to be tested deposits, the unevenness of the amount deposited on the surfaces of the test reagent layer and the tone layer for criterion can occur to generate color formation hindrance and color spots even if wetting of the test reagent layer with the solution to be tested is identical with that of the tone layer for criterion as described above.

In the present invention, the problems described above can be solved by providing the highly water-absorptive portion at the surface of said substrate in the vicinity of the test reagent layer and the tone layer to quickly absorb and remove excess solution to be tested deposited on the test reagent layer and the tone layer, thereby uniformly depositing the solution to be tested.

Such highly water-absorptive portions may be provided on the substrate so that they come into contact with either or both the test reagent layer and the tone layer. Alternatively, the highly water-absorptive portions may be spaced apart from the layers. The highly water-absorptive portions may surround both layers. The position and shape of the highly water-absorptive portion are not critical. The highly water-absorptive portion is formed in the vicinity of the test reagent layer and the tone layer so that excess solution to be tested deposited on said layers can be absorbed.

The highly water-absorptive portion can be preferably formed by printing an ink composition containing a highly water-absorptive material as with test reagent and tone layers described hereinafter. Such an ink composition contains water-absorptive powders such as cellulose, starch and highly water-absorptive gels; hydrophilic or hydrophobic resins; binders; additives such as inorganic fillers for forming a porous film; and solvents. Examples of the highly water-absorptive gels which are used in the present invention include polyvinyl alcohol (PVA), and crosslinked and grafted copolymers based on acrylate, acrylonitrile, starch or the like. Examples of commercially available highly water-absorptive gels include Sumika Gel SP 520 having a water-absorptive capacity of 600 times (a PVA-acrylate block copolymer available from Sumitomo Kagaku Kogyho, K.K., Japan), Sun Wet IM-1000 having a water-absorptive capacity of 1,000 times (acrylic acid grafted starch available from Sanyo Kasei, K.K., Japan), and KI Gel having a water-absorptive capacity of 1,000 times (a reaction product of PVA with a cyclic acid anhydride).

Form

The test device for body fluids according to the present invention can be formed in the form of sheets, sticks, rolls, tapes or the like. Alternatively, the test device for body fluids may be formed in forms wherein the substrate per se can sample the solution to be tested, for example, in the form of cups, test tubes, dishes, trays and droping pipettes. With respect to the arrangement of the tone layer and the test reagent layer, it is particularly preferable that these layers be provided via a constant interval, for example, of from 0.2 to 2 mm as shown in FIG. 1.

That is, even if wetting of the test reagent layer and the tone layer for criterion with the solution to be tested is uniform, the deposited body to be tested migrates between both layers when they are provided on the substrate so that the test reagent layer comes into contact with the tone layer. In this case, the color of the boundary portion changes and it is difficult to compare the tone of the tone layer with the color of the reagent layer. Further, when the excess solution to be tested deposits on both layers, particularly the test reagent layer, the unevenness of the amount of the layer surface deposited occurs to generate color formation hindrance and color spots. However, such problems can be solved by utilizing the arrangement as described above.

While the gap between the test reagent layer and the tone layer for criterion is not limited to 0.2-2 mm described above, it is preferable. If the interval is less than 0.2 mm, the boundary between the test reagent layer and the tone layer cannot distinctly be judged by visual observation. When the solution to be tested deposits, it is impossible to prevent mutual interference due to reasons such as the migration of the ingredients between the test reagent layer and the tone layer. On the other hand, if the gap between the test reagent layer and the tone layer is more than 2 mm, it is difficult to compare the color of the test reagent layer with the tone of the tone layer, and the effect obtained by providing the tone layer in the vicinity of the test reagent layer will be reduced.

Embodiments of test devices for body fluids according to the present invention other than the embodiment shown in FIG. 1 will be described with reference to the Drawings.

Figure 6:
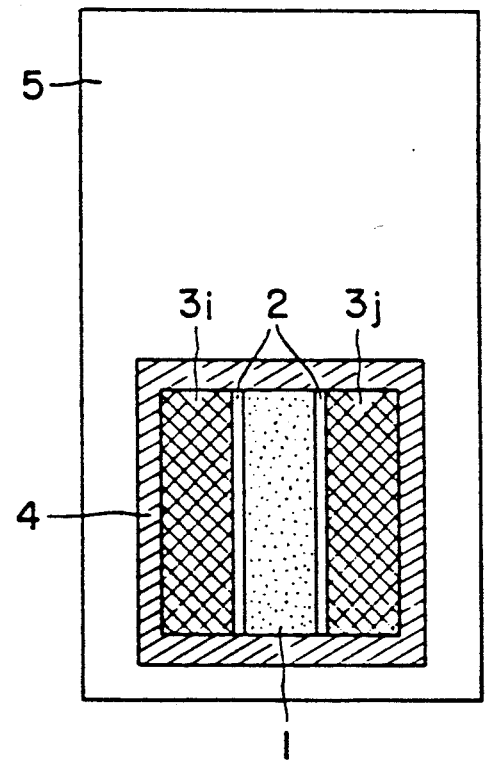

FIG. 2 shows a test device for body fluids wherein, for example, a test reagent layer for glucose detection 1 is provided on a substrate 5; wherein tone layers for criterion 3a, 3b, 3c, 3d, 3e and 3f showing each color of the test reagent layer at each concentration of glucose in a specimen ranging from 0 to a specific concentration respectively are provided by affixation or printing so that they are spaced apart from the test reagent layer at a slight gap 2; and wherein a highly water-absorptive portion 4 is provided adjacent to the test reagent layer 1. When a test is carried out using such a test paper, it is possible to prevent mutual interference of each ingredient in both layers and the boundary of both layers is distinct because the gap 2 is provided between the test reagent layer 1 and the tone layers 3a–3f. Further, since the highly water-absorptive portion 4 absorbs the solution to be tested which excessively deposits on the test reagent, layer, the solution to be tested does not downwardly flow the reagent layer and does not reside in the reagent layer in picking up the test paper. Thus, the resulting color does not become uneven, and semiquantitative determination of the concentration of a material to be tested in the solution to be tested can be accurately carried out. Further, as shown in FIG. 4, a test reagent layer 1 and a tone layer for criterion 3 disposed so that it surrounds the test reagent layer 1 at a gap 2 are provided on a substrate 1. Furthermore, as shown in FIG. 4, a highly water-absorptive portion 4 is provided at the periphery of the tone layer 3 at an interval. In this embodiment, when the tone of the tone layer 3 is set so that it shows that the concentration of a material to be tested in a solution to be tested is the upper limit of a normal range, the immersion of the test device for body fluids in a specimen makes it possible to easily judge whether the concentration of the material to be tested in the specimen is within the normal range or not. The provision of the highly water-absorptive portion at the periphery of the test reagent layer and the tone layer can prevent the excess specimen deposited on the substrate from downwardly flowing and penetrating, the deposition of the solution to be tested becomes uniform, and accurate judgment becomes possible. FIG. 3 shows a test device for body fluids wherein a test reagent layer 1 and a tone layer 3 are provided at a gap 2 as in FIG. 1 except that the highly water-absorptive portion 4 shown in FIG. 1 is not provided. When the substrate 1 having good drainage is used, the test device for body fluids can have such a structure. Further, as shown in FIGS. 5 and 6, tone layers for criterion are divided into two tone layer 3g and 3h or 3i and 3j so that a test reagent layer 1 is sandwiched therebetween. The test reagent layer and the tone layers are provided at gaps 2. Further, highly water-absorptive portions 4a and 4b can be provided so that they are adjacent to the test reagent layer 1 and the tone layers 3g and 3h. A highly water-absorptive portion 4 can be provided so that it surrounds the test reagent layer 1 and the tone layers 3i and 3j. According to these structures, the same effect as described above is obtained.

FIGS. 5 and 6 show test devices for judging whether the concentration of the material to be tested in the solution to be tested is within the adequate range or not. For example, the test devices shown in FIGS. 5 and 6 are suitable for judgment of a blood sugar value or the like. That is, it is possible to accurately judge whether the blood sugar value is within an adequate range by providing, on a substrate 5, tone layers for criterion sandwiching a test reagent layer 1, said tone layers consisting of a tone layer 3g or 3i having a tone which adequate range, and a tone layer 3h or 3j having a tone which exhibits a concentration which is the upper limit of the adequate range.

Figure 7:
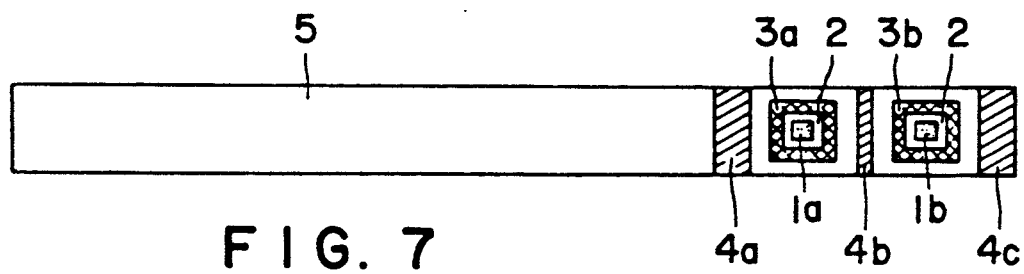

FIG. 7 shows a test device for body fluid wherein two test reagent layers 1a and 1b capable of testing mutually different two test items and tone layers 3a and 3b are provided on a substrate 5 via gaps 2; wherein a highly water-absorptive portion 4b is provided between the test reagent layers; and wherein highly water-absorptive portions 4a and 4c are provided at the start and end of an array of the aligned test reagent layers, respectively.

Figure 8:
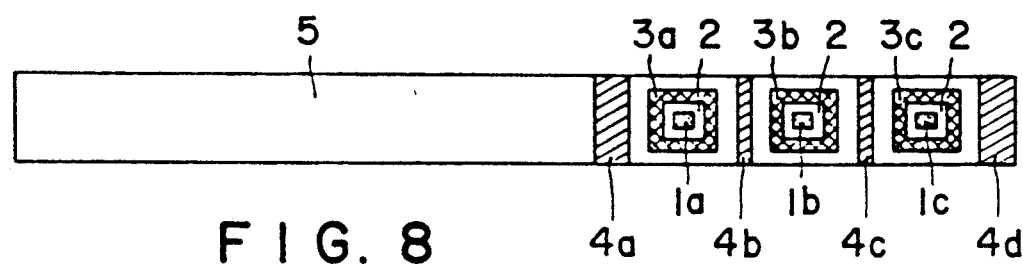

FIG. 8 shows a test device for body fluids having three test reagent layers 1a, 1b and 1c, tone layers 3a, 3b and 3c, and highly water-absorptive portions 4a, 4b, 4c and 4d. Mutually different test items can be tested by the test device shown in FIG. 8.

While any of the embodiments described above are the preferred embodiments of the present invention, the test devices for body fluids according to the present invention include embodiments other than the embodiments described above. For example, test devices (not shown) having the structures shown in FIGS. 1 through 6 except that the highly water-absorptive portion 4 and the gap 2 are not provided are within the scope of the present invention.

Further, in the test device for body fluids according to the present invention, at least two test reagent layers capable of testing a plurality of test items and a plurality of tone layers for criterion corresponding to these test reagent layers may be provided in one test device for body fluids. While combinations of test items examined in this test device for body fluids are not restricted, examples of two items include a combination of glucose and protein, and a combination of urobilinogen and protein, and examples of three items include a combination of glucose, protein and pH, and the like.

While examples of the present invention are described below, the present invention is not limited to the description of these examples.

EXAMPLE A-1

A test device as shown in FIG. 2 (without any highly water-absorptive portion) was produced according to the following process:

Production of Test Reagent Layers

Test reagent solutions having the following composition were prepared, and filler papers (manufactured by Toyo Roshi, Japan; No. 51) were impregnated with these test reagent solutions. The impregnated filter papers were dried for 2 hours at 50° C. to produce test reagent layers.

| Glucose test reagent solution: | |
|---|---|
| Glucose oxidase (manufactured by Toyobo, Japan; Grade II) | 0.6 part by wt. |
| Peroxidase (manufactured by Toyobo, Japan; Grade III) | 0.15 part by wt. |
| o-Tolidine dihydrochloride | 0.5 part by wt. |
| Citric acid/sodium citrate buffer (a pH of 5.5) | 80 parts by wt. |
| Gelatin aqueous solution (5%) | 50 parts by wt. |
| Distilled water | 20 parts by wt. |
| Ethyl alcohol | 30 parts by wt. |

Production of Tone Layers

Normal urine and solutions obtained by dissolving beta-D-glucose in normal urine so that its concentrations were 50 milligrams per deciliter, 100 milligrams per deciliter, 250 milligrams per deciliter, 500 milligrams per deciliter, and 2,000 milligrams per deciliter were used as solutions to be tested, and the test reagent layers obtained as described above were immersed in the solutions to be tested, thereafter immediately removed, and allowed to stand for one minute, and the color of each test reagent layer was observed.

Filter papers (manufactured by Toyo Roshi, Japan; No. 51) were impregnated with the following compositions having oil-soluble dyes dissolved or dispersed, and the impregnated filter papers were dried for 2 hours 50° C. to product tone layers. The type and amount of disperse dyes used in the production of each tone layer were set so that the tone formed by impregnating the filter paper with the following composition and disperse dye to obtain the tone layer, immersing the tone layer in the solution to be tested, thereafter immediately removing it and allowing to stand for one minute was consistent with the color of the test reagent layer described above. Composition for a glucose tone layer:

| | |
|---|---|
| Sorbitan monolaurate (manufactured by Kao Sekken, Japan; Span 20) | 14.4 parts by wt. |
| Citric acid | 2.8 parts by wt. |
| Sodium citrate | 11.0 parts by wt. |
| Polyvinyl pirrolidone (manufactured by BASF; Koridone 90) | 12.6 parts by wt. |
| Polyvinyl butyral (manufactured by Sekisui Kagaku, Japan; Eslec BX-1) | 2.25 parts by wt. |
| Cellulose fine powder (manufactured by Asahi Kasei, Japan; Abicel TG-D) | 171 parts by wt. |
| n-Amyl alcohol | 171 parts by wt. |
| Butyl cellosolve acetate | 50 parts by wt. |
| Oil-soluble dyes: | |
| Black dye (manufactured by Nippon Kayaku, Japan; Kayaset Black 151 H) | minor amount |
| Blue dye (manufactured by Nippon Kayaku, Japan; Kayaset Blue 814) | minor amount |
| Red dye (manufactured by Nippon Kayaku, Japan; Kayaset Red 802) | minor amount. |

Production of Test Devices

The test devices for body fluids as shown in FIG. 2 were produced by affixing a test reagent layer 1 cut into a 5 mm × 30 mm tetragon to a 300 μ thick white polystyrene sheet which was a substrate 5, and affixing the portions 3a, 3b, 3c, 3d, 3e and 3f of the tone layer 3 in the vicinity of the test reagent layer 1, said portions 3a, 3b, 3c, 3d, 3e and 3f being obtained by cutting the tone layer 3 into tetragons having each side of 5 mm and said tone layer 3 showing that the concentrations of beta-D-glucose in the specimens obtained by preparing as described above were 0.50 milligram per deciliter, 100 milligrams per deciliter, 250 milligrams per deciliter, 500 milligrams per deciliter and 2,000 milligrams per deciliter.

Normal urine and solutions obtained by dissolving beta-D-glucose in normal urine so that its concentrations were 50 milligrams per deciliter, 100 milligrams per deciliter, 250 milligrams per deciliter, 500 milligrams per deciliter, and 2,000 milligrams per deciliter were used as solutions to be tested, the resulting test devices were immersed in the respective solutions to be tested, thereafter immediately removed and allowed to stand for one minute, and their colors were observed. For each solution to be tested, the color of the test reagent layer 1 was completely consistent with the tone of any of the portions 3a, 3b, 3c, 3d, 3e and 3f of the tone layer 3 exhibiting the corresponding concentrations of the solutions to be tested.

COMPARATIVE EXAMPLE A-1

Production of Test Reagent Layers

The test reagent layers were produced as in Example A-1.

Production of Tone Layers

Solutions to be tested which have been prepared as in Example A-1 were used, the test reagent layers were immersed in the solutions to be tested, thereafter immediately removed and allowed to stand for one minute, and the color of each test reagent layer was observed. The tone layers 3a-3f having tones consistent with the colors of the test reagent layers described above were produced by screen printing screen process ink (manufactured by Teikoku Ink, Japan; VG) onto a 300 μ thick white polystyrene sheet which was a substrate 5 so that tetragons having each side of 5 mm were formed.

Production of Test Devices

The test devices shown in FIG. 2 were produced by affixing the test reagent layer cut into a 5 mm × 30 mm tetragon in the vicinity of the tone layers 3a-3f obtained by the screen printing described above.

Beta-D-glucose-containing solutions to be tested which have been prepared as in Example A-1 were used, the resulting test papers for inspection were immersed in the respective solutions to be tested, thereafter immediately removed and allowed to stand for one minute, and their colors were observed. The test reagent layers uniformly absorbed the solutions to be tested, whereas the solutions to be tested deposited on the tone layers in the form of droplets. Accordingly, for each solution to be tested, the color of the test reagent layer was not consistent with the tone of the tone layer exhibiting the corresponding concentration of the solution to be tested.

EXAMPLE A-2

Production of Test Reagent Layers

The test reagent layers 1 were produced by finely dispersing a test reagent composition comprising the following ingredients in a homomixer and thereafter printing it onto a 300 μ thick white polystyrene sheet which was a substrate 5 shown in FIG. 2 by screen printing so that a 5 mm × 30 mm tetragon was formed. A screen plate used was of 80 mesh, and the sum of the thickness of a resist and a screen gauze was 130 μm.

| Composition for a glucose test reagent layer: | |
|---|---|
| Glucose oxidase (manufactured by Toyobo, Japan, Grade II) | 3.6 parts by wt. |
| Peroxidase (manufactured by Toyobo, Japan; Grade III) | 2.4 parts by wt. |
| Guaiacum resin | 4.8 parts by wt. |
| Sorbitan Monolaurate (manufactured by Kao Sekken, Japan; Span 20) | 7.2 parts by wt. |
| L-Ascorbyl stearate | 0.24 part by wt. |
| Citric acid | 2.8 parts by wt. |
| Sodium citrate | 11.0 parts by wt. |
| Polyvinyl pyrrolidone (manufactured by BASF; Koridone 90) | 12.6 parts by wt. |
| Polyvinyl butyral (manufactured by Sekisui Kagaku, Japan; Eslec BX-1) | 2.25 parts by wt. |
| Cellulose fine powder (manufactured by Asahi Kasei, Japan; Abicel TG-D) | 171 parts by wt. |
| n-Amyl alcohol | 171 parts by wt. |
| Butyl cellosolve acetate | 67 parts by wt. |

The resulting printed matter was dried for 40 minutes at 60° C. to obtain test devices.

Production of Tone Layers and Production of Test Devices

Normal urine and solutions obtained by dissolving beta-D-glucose in normal urine so that its concentrations were 50 milligrams per deciliter, 100 milligrams per deciliter, 250 milligrams per deciliter, 500 milligrams per deciliter, and 2,000 milligrams per deciliter were used as solutions to be tested, the test reagent layers obtained as described above were immersed in the solutions to be tested, thereafter immediately removed and allowed to stand for one minute, and the color of each test reagent layer was observed.

The tone layers were then obtained by setting the type and amount of disperse dyes so that the tone obtained by immersing the resulting tone layer in the solution to be tested, thereafter immediately removing and allowing to stand for one minute were consistent with the color of each test reagent layer described above. That is, test devices as shown in FIG. 2 were produced by dissolving/dispersing disperse dyes in the following composition for tone layers which has been obtained by finely dispersing in a homomixer; screen printing the resulting mixture onto a white polystyrene sheet substrate 5 in the vicinity of the test reagent layer 1 so that there were formed tetragons 3a, 3b, 3c, 3d, 3e and 3f (each side being 5 mm) constituting the tone layer 3 that the concentrations of beta-D-glucose in the specimen were 0.50 milligram per deciliter, 100 milligrams per deciliter, 250 milligrams per deciliter, 500 milligrams per deciliter, and 2,000 milligrams per deciliter; and drying the resulting printed matter for 40 minutes at 60° C. A screen plate used was of 80 mesh, and the sum of a resist and a screen gauze was 130 μ.

A composition for tone layers is similar to that described in Example A-1.

Normal urine and solutions obtained by dissolving beta-D-glucose in normal urine so that its concentrations were 50 milligrams per deciliter, 100 milligrams per deciliter, 250 milligrams per deciliter, 500 milligrams per deciliter, and 2,000 milligrams per deciliter were used as solutions to be tested, the resulting test devices were immersed therein, thereafter immediately removed and allowed to stand for one minute, and their colors were observed. For each solution to be tested, the color of the test reagent layer 1 was completely consistent with the tone of any of the portions 3a, 3b, 3c, 3d, 3e and 3f of the tone layer 3 showing the corresponding concentrations of the solutions to be tested.

COMPARATIVE EXAMPLE A-2

Production of Test Reagent Layers

The test reagent layers were produced as in Example A-2.

Production of Tone Layers and Production of Test Devices

Solutions to be tested which have been prepared as in Example A-2 were used, test reagent layers obtained as in Example A-2 as described above were immersed in the solutions to be tested, thereafter immediately removed and allowed to stand for one minute, and the color of each test reagent layer was observed.

The test devices shown in FIG. 2 (excluding the highly water-absorptive portion 4) were produced by screen printing screen process ink (manufactured by Teikoku Ink, Japan; VG) onto a 300 μ thick white polystyrene sheet which was a substrate in the vicinity of the test reagent layer 5 so that tetragons having each side of 5 mm were formed to produce tone layers 3a–3f having tones consistent with the color of each test reagent layer described above.

Beta-D-glucose-containing solutions to be tested which have been prepared as in Example A-2 were used, the resulting test papers for inspection were immersed in the respective solutions to be tested, thereafter immediately removed and allowed to stand for one minute, and their colors were observed. The test reagent layers uniformly absorbed the solutions to be tested, whereas the solutions to be tested deposited on the tone layers in the form of droplets. Accordingly, for each solution to be tested, the color of the test reagent layer was not consistent with the tone of the tone layer exhibiting the corresponding concentration of the solution to be tested.

EXAMPLE A-3

Production of a Test Reagent Layer

The test reagent layer 1 was produced as in Example A-2 except that the test reagent layer was printed onto a 300 μ thick white polystyrene sheet which was a substrate 5 so that a 5 mm×5 mm tetragon was formed.

Production of Tone Layers and Production of Test Devices

A solution obtained by dissolving beta-D-glucose in normal urine so that its concentration was 50 milligrams per deciliter was used as a solution to be tested, the test reagent layer obtained as described above was immersed in the solution to be tested, thereafter immediately removed and allowed to stand for one minute, and the color of the test reagent layer was observed.

The test devices shown in FIG. 1 (excluding the highly water-absorptive portions 4a and 4b) were produced by preparing the tone layer 3 as in Example A-2 except that the tone layer 3 was formed by printing so that a tetragon having each side of 15 mm and having a central tetragonal notch having each side of 5 mm was formed. The type and quantity of disperse dyes were set so that the tone obtained by immersing the resulting tone layer in the solution to be tested, thereafter immediately removing and allowing to stand for one minute, was consistent with the color of the test reagent layer described above.

Normal urine and solutions obtained by dissolving beta-D-glucose in normal urine so that its concentrations were 50 milligrams per deciliter and 100 milligrams per deciliter were used as solutions to be tested, the resulting test papers for inspection were immersed in the respective solutions, thereafter immediately removed and allowed to stand for one minute, and their colors were observed. When the concentration of beta-D-glucose in the solution to be tested was 50 milligrams per deciliter, the color of the test reagent layer was completely consistent with the tone of the tone layer. When the solution to be tested was normal urine or when the concentration of beta-D-glucose in the solution to be tested was 100 milligrams per deciliter, the color of the test reagent layer could be distinctly distinguished from the tone of the tone layer.

COMPARATIVE EXAMPLE A-3

Production of a Tone Layer

A solution to be tested which has been prepared as in Example A-3 was used, a test reagent layer described below was immersed in the solution to be tested, thereafter immediately removed and allowed to stand for one minute, and the color of the test reagent layer was observed.

The tone layer having a tone consistent with the color of the test reagent layer described above was produced by screen printing screen process ink (manufactured by Teikoku Ink, Japan; VG) onto a 300 μ thick white polystyrene sheet so that a tetragon having each side of 15 mm was formed.

Production of a Test Reagent Layer and Production of a Test Device

The test device shown in FIG. 2 (without any highly water-absorptive portion 4) was produced by preparing the test reagent layer 1 as in Example A-3 except that the test reagent layer having a 5 mm×5 mm tetragon was formed on the tone layer 2 by printing.

A solution to be tested which has been prepared as in Example A-3 and which contained beta-D-glucose at a level of 50 milligrams per deciliter was used, the resulting test paper for inspection was immersed in the solution to be tested, thereafter immediately removed and allowed to stand for one minute, and its color was observed. When the concentration of beta-D-glucose in the solution to be tested was 50 milligrams per deciliter, the test reagent layer uniformly absorbed the solution to be tested, whereas the solution to be tested deposited on the tone layer in the form of droplets and therefore the color of the test reagent layer was not consistent with the tone of the tone layer.

EXAMPLE A-4

Production of a Test Reagent Layer

A test reagent composition comprising the following ingredients was finely dispersed in a homomixer, and the test reagent layer 1 was printed onto a 300 μ thick white polyethylene sheet which was a substrate 5 by screen printing so that a 5 mm×15 mm tetragon was formed as shown in FIG. 6 (without any highly water-absorptive portion 4). A screen plate used was of 80 mesh, and the sum of the thickness of a resist and a screen gauze was 190 μ.

| Composition for a protein test reagent: | |
|---|---|
| Tetrabromophenol Blue | 0.40 part by wt. |
| Citric acid | 25.7 parts by wt. |
| Sodium citrate | 11.0 parts by wt. |
| Sorbitan monolaurate (manufactured by Kao Sekken, Japan; Span 20) | 4.0 parts by wt. |
| Sodium carboxymethyl cellulose (manufactured by Whatman; CM-32) | 50.0 parts by wt. |
| Calcium carboxymethyl cellulose (Daiseru Kagaku, Japan) | 10.0 parts by wt. |
| Amyl alcohol esterification product of methyl vinyl ether-maleic anhydride copolymer (manufactured by G.A.F.; Gantrez AN-169) | 4.97 parts by wt. |
| Cellulose fine powder (manufactured by Asahi Kasei, Japan; Abicel TG-D) | 108 parts by wt. |
| n-Amyl alcohol | 28.1 parts by wt. |
| Butyl cellosolve | 107.7 parts by wt. |
| Butyl cellosolve acetate | 50.2 parts by wt. |

The resulting printed matter was dried for 30 minutes at 60° C. to obtain the test reagent layer 1.

Production of Tone Layers and Production of a Test Device

A solution obtained by dissolving bovin serum albumin in normal urine so that its concentration was 15 milligrams per deciliter was used as a solution to be tested, the test reagent layer obtained as described above was immersed in the solution to be tested, thereafter immediately removed and allowed to stand for one minute, the color of the test reagent layer was observed.

The test device shown in FIG. 6 was produced by dissolving/dispersing disperse dyes in the following composition for tone layers which has been finely dispersed in a homomixer, screen printing the resulting mixture on a substrate 5 in the vicinity of the test reagent layer 1 provided as described above so that 5 mm × 15 mm tetragons 3i and 3j having a 5 mm × 15 mm central tetragonal notch were formed, and drying the resulting printed matter for 30 minutes at 60° C. A screen plate used was of 80 mesh, and the sum of the thickness of a resist and a screen gauze was 190 μ. The type and amount of disperse dyes were set so that the tone obtained by immersing the resulting tone layers in the solution to be tested, thereafter immediately removed and allowed to stand for one minute was consistent with the color of the test reagent layer described above.

| Composition for protein tone layers: | |
|---|---|
| Sorbitan monolaurate (manufactured by Kao Sekken, Japan; Span 20) | 4.0 parts by wt. |
| Sodium carboxymethyl cellulose (manufactured by Whatman; CM-32) | 50.0 parts by wt. |
| Calcium carboxymethyl cellulose (manufactured by Daiseru Kagaku, Japan) | 10.0 parts by wt. |
| Amyl alcohol esterification product of methyl vinyl ether-maleic anhydride copolymer (manufactured by G.A.F.; Gantrez AN-169) | 4.97 parts by wt. |
| Cellulose fine powder (manufactured by Asahi Kasei, Japan; Abicel TG-D) | 40 parts by wt. |
| n-Amyl alcohol | 28.1 parts by wt. |
| Butyl cellosolve | 28 parts by wt. |
| Butyl cellosolve acetate | 38 parts by wt. |
| Oil-soluble dyes: | |
| Yellow dye (manufactured by Nippon Kayaku, Japan; Kayaset Yellow 937) | minor amount |
| Blue dye (manufactured by Nippon Kayaku, Japan; Kayaset Blue 814) | minor amount |

Normal urine and solutions obtained by dissolving bovine serum albumin in normal urine so that its concentrations were 15 milligrams per deciliter and 30 milligrams per deciliter were used as solutions to be tested, the resulting test papers for inspection were immersed in the solutions to be tested, thereafter immediately removed and allowed to stand for one minute, and their colors were observed.

When the concentration of bovine serum albumin in the solution to be tested was 15 milligrams per deciliter, the colors of the test reagent layer 1 were completely consistent with the tones of the tone layers 3i and 3j. When the solution to be tested was normal urine or when the concentration of bovine serum albumin in the solution to be tested was 30 milligrams per deciliter, the colors of the test reagent layers 1 could be distinctly distinguished from the tones of the tone layers 3i and 3j.

COMPARATIVE EXAMPLE A-4

Production of Test Reagent Layers

The test reagent layers were produced as in Example A-4.

Production of Tone Layers and Production of Test Devices

Solutions to be tested which have been prepared as in Example A-4 were used, the resulting test reagent layers were immersed in the solutions to be tested, thereafter immediately removed and allowed to stand for one minute, and the colors of the test reagent layers were observed.

Test devices shown in FIG. 6 (without any highly water-absorptive portion 4) were produced by screen printing screen process ink (manufactured by Teikoku Ink, Japan, VG) in the vicinity of the test reagent layer 1 printed onto a 300 μ thick white polystyrene sheet which was a substrate 5 so that a 5 mm × 15 mm tetragon was formed such that 5 mm × 15 mm tetragons 3i and 3j having a 5 mm × 15 mm central tetragonal notch were formed to produce the tone layers 3i and 3j having tones consistent with the colors of the test reagent layer 1.

The solutions to be tested which have been prepared as Example A-4 were used, the resulting test papers for inspection were immersed in the solutions to be tested, thereafter immediately removed and allowed to stand for one minute, and their colors were observed. When the concentration of bovine serum albumin in the solution to be tested was 15 milligrams per deciliter, the test reagent layer 1 uniformly absorbed the solutions to be tested, whereas the solutions to be tested deposited on the tone layers 3i and 3j in the form of droplets and therefore the colors of the test reagent layer 1 were not consistent with the tones of the tone layers 3i and 3j.

EXAMPLE A-5

Production of Test Reagent Layers

A test reagent composition was prepared by dissolving/dispersing the following reagent composition excluding 0.098 part by weight of sodium hydroxide and 2 parts by weight of water in a homomixer, thereafter adding a solution of 0.098 part by weight of sodium hydroxide in 2 parts by weight of water, and thoroughly dissolving/dispersing the resulting mixture in a homomixer.

| Composition for a pH test reagent: | |
| --- | --- |
| Sodium hydroxide | 0.088 part by wt. |
| Water | 2 parts by wt. |
| Methyl Red | 0.070 parts by wt. |
| Bromothymol Blue | 1.0 part by wt. |
| Dodecyltrimethyl ammonium chloride | 1.0 part by wt. |
| Polyvinyl pyrrolidone (manufactured by BASF; Kolidone 90) | 8.3 parts by wt. |
| Polyvinyl butyral (manufactured by Sekisui Kagaku, Japan; Eslec BX-1) | 4.1 parts by wt. |
| Cellulose fine powder (manufactured by Asahi Kasei, Japan; Abicel TG-D) | 174 parts by wt. |
| Butyl cellosolve | 226 parts by wt. |
| Butyl cellosolve acetate | 22 parts by wt. |

The resulting test reagent composition was printed onto a 300 μ thick white polystyrene sheet which was a substrate 5 shown in FIG. 2 by screen printing so that a 5 mm×25 mm tetragon was formed. A screen plate used was of 80 mesh, and the sum of the thickness of a resist and a screen gauze was 190 μ. The resulting printed matter was dried for 30 minutes at 60° C. to obtain the test reagent layers 1.

Production of Tone Layers and Production of Test Devices

Those obtained by adjusting the pH of normal urine with hydrochloric acid or sodium hydroxide to pHs of 5, 6, 7, 8 and 9 respectively were used as solutions to be tested, the test reagent layers were immersed in the solutions to be tested, thereafter immediately removed and allowed to stand for one minute, and their colors were observed.

The test devices shown in FIG. 2 (without any highly water-absorptive portion 4) were produced by dissolving/dispersing disperse dyes in the following composition for tone layer finely dispersed in a homomixer; thereafter screen printing the solution or dispersion in the vicinity of the test reagent layer 1 so that there were formed tetragons 3a, 3b, 3c, 3d, 3e, and 3f having each side of 5 mm and constituting a tone layer 2 exhibiting that the pHs of the solutions to be tested were 5, 6, 7, 8 and 9; and drying the resulting printed matter for 30 minutes at 60° C. A screen plate used was of 80 mesh, and the sum of the thickness of a resist and a screen gauze was 190 μ. The type and quantity of disperse dyes were set so that the tones obtained by immersing the resulting tone layer in the solutions to be tested, thereafter immediately removed and allowed to stand for one minute were consistent with the colors described above.

| Composition for a pH tone layer: | |
| --- | --- |
| Polyvinyl pyrrolidone (manufactured by BASF; Kolidone 90) | 8.3 parts by wt. |
| Polyvinyl butyral (manufactured by Sekisui Kagaku, Japan; Eslec BX-1) | 4.1 parts by wt. |
| Cellulose fine powder (manufactured by Asahi Kasei, Japan; Abicel TG-D) | 174 parts by wt. |
| Butyl cellosolve | 226 parts by wt. |
| Butyl cellosolve acetate | 22 parts by wt. |
| Oil-soluble dyes: | |
| Yellow dye (manufactured by Nippon Kayaku, Japan; Kayaset Yellow 937) | minor amount |
| Red dye (manufactured by Nippon Kayaku, Japan; Kayaset Red 802) | minor amount |
| Blue dye (manufactured by Nippon Kayaku, Japan; Kayaset Blue 814) | minor amount |
| Black dye (manufactured by Nippon Kayaku, Japan; Kayaset Black 151 H) | minor amount |

In the meanwhile, the red dye and the yellow dye were used under acidic conditions, and the yellow dye, blue dye, and the black dye were used under alkaline conditions.

Those obtained by adjusting the pH of normal urine with hydrochloric acid or sodium hydroxide to pHs of 5, 6, 7, 8 and 9 respectively were used as solutions to be tested, the resulting test papers for inspection 4 were immersed in the solutions to be tested, thereafter immediately removed and allowed to stand for one minute, and their colors were observed. For each solution to be tested, the color of the test reagent layer 1 was completely consistent with the tone of any of the portions 3a, 3b, 3c, 3d, 3e and 3f of the tone layer 3 exhibiting the corresponding pHs of the solutions to be tested.

COMPARATIVE EXAMPLE A-5

Production of Test Reagent Layers

The test reagent layers were produced as in Example A-5.

Production of Tone Layers and Production of Test Devices

Solutions to be tested which have been prepared as in Example A-5 were used, the resulting test reagent layers were immersed in the solutions to be tested, thereafter immediately removed and allowed to stand for one minute, and their colors were observed.

The test devices as shown in FIG. 2 were produced by screen printing screen process ink (manufactured by Teikoku Ink, Japan; VG) in the vicinity of the test reagent layer so that tetragons having each side of 5 mm were formed to produce the tone layers 3a-3f having tones consistent with the colors of each test reagent layer described above. The solutions to be tested which have been prepared as in Example A-5 were used, the resulting test papers for inspection were immersed in the respective solutions to be tested, thereafter immediately removed and allowed to stand for one minute, and their colors were observed. The test reagent layers uniformly absorbed the solutions to be tested, whereas the solutions to be tested deposited on the tone layers in the form of droplets. Accordingly, for each solution to be tested, the color of the test reagent layer was not consistent with the tone of the tone layer exhibiting the corresponding pH of the solution to be tested.

EXAMPLE B-1

Test devices for body fluids shown in FIG. 1 (without any highly water-absorptive portions 4a and 4b) were produced as in examples described above using the following composition for forming a test reagent layer and the following composition for forming a tone layer.. Composition for forming a test reagent layer for occult blood detection:

| | |
|---|---|
| Cumene hydroperoxide | 3.6 parts by wt. |
| 6-Methoxyquinoline | 1.0 part by wt. |
| (The above ingredients being present in capsules) | |
| Gum arabic | 9.4 parts by wt. |
| 3,3',5,5'-Tetramethyl benzidine | 1.5 parts by wt. |
| Citric acid | 0.56 part by wt. |
| Sodium citrate | 2.2 parts by wt. |
| Titriethanolamine lauryl sulfate | 1.62 parts by wt. |
| Polyethylene glycol | 2.52 parts by wt. |
| Polyvinyl butyral (manufactured by Sekisui Kagaku, Japan; Eslec BX-1) | 3.6 parts by wt. |
| Cellulose fine powder (manufactured by Asahi Kasei, Japan; Abicel TG-D) | 22.4 parts by wt. |
| n-Amyl alcohol | 39.7 parts by wt. |
| Butyl cellosolve acetate | 13.0 parts by wt. |
| Composition for forming a tone layer: | |
| Gum arabic | 9.4 parts by wt. |
| Citric acid | 0.56 part by wt. |
| Sodium citrate | 2.2 parts by wt. |
| Polyethylene glycol | 2.52 parts by wt. |
| Polyvinyl butyral (manufactured by Sekisui Kagaku, Japan,; Eslec BX-1) | 3.6 parts by wt. |
| Cellulose fine powder (manufactured by Asahi Kasei, Japan; Abicel TG-D) | 22.4 parts by wt. |
| n-Amyl alcohol | 39.7 parts by wt. |
| Butyl cellosolve acetate | 13.0 parts by wt. |
| Oil soluble dyes: | |
| Yellow dye (manufactured by Nippon Kayaku, Japan; Kayaset Yellow 937) | minor amount |
| Blue dye (manufactured by Nippon Kayaku, Japan; Kayaset Blue 814) | minor amount |

EXAMPLE B-2

A composition for urobilinogen detection comprising the following ingredients and a composition for tone layer comprising the following ingredients were prepared by fine dispersion by means of a high speed stirrer, thereafter a square having each side of 5 mm was printed onto a 300 μm thick white polystyrene sheet by screen printing, and it was dried for 30 minutes at a temperature of 40° C. after printing. The screen ruling of the plate used in printing was of 80 mesh, and the sum of the thickness of a resist and a screen gauze was 180 μm. After drying, the printed matter was cut into specific dimension to obtain a test device as shown in FIG. 1 (without any highly water-absorptive portion 4).

| | |
|---|---|
| Composition for urobilinogen detection: | |
| Para-dimethylamino benzaldehyde | 2.45 parts by wt. |
| Sulfosalicylic acid | 125 parts by wt. |
| Sodium laurate | 2.40 parts by wt. |
| Sorbitan monolaurate | 1.3 parts by wt. |
| (its HLB being 8.6) | |
| Caffeine | 16 parts by wt. |
| Amyl alcohol half ester of methyl vinyl ether-maleic anhydride copolymer (manufactured by GAF; Gantrez AN-169) | 75 parts by wt. |
| Ethylene glycol monomethyl ether | 121 parts by wt. |
| Ethylene glycol monomethyl ether acetate | 125 parts by wt. |
| Sodium carboxymethyl cellulose | 31 parts by wt. |
| Microcrystalline cellulose (manufactured by Asahi Kase, Japan; Abicel TG-D) | 156 parts by wt. |
| Composition for forming a tone layer: | |
| Sulfosalicylic acid | 125 parts by wt. |
| Caffeine | 16 parts by wt. |
| Sorbitan monolaurate | 1.3 parts by wt. |
| Amyl alcohol esterification product of methyl vinyl ether-maleic anhydride copolymer (manufactured by GAF; Gantrez AN-169) | 11 parts by wt. |
| Methyl cellosolve | 121 parts by wt. |
| Methyl cellosolve acetate | 125 parts by wt. |
| Sodium carboxymethyl cellulose | 31 parts by wt. |
| Cellulose fine powder (manufactured by Asahi Kase, Japan; Abicel TG-7) | 156 parts by wt. |
| Amyl alcohol | 64 parts by wt. |
| Oil-soluble dyes: | |
| Yellow dye (manufactured by Nippon Kayaku, Japan; Kayaset Yellow 937) | minor amount |
| Red dye (manufactured by Nippon Kayaku; Kayaset Red 802) | minor amount |
| Black dye (manufactured by Nippon Kayaku, Japan; Kayaset Black 151H) | minor amount |

The following three solutions to be tested were provided:
(1) Normal urine;
(2) Urine containing urobilinogen at a level of 1 EU/dl; and
(3) Urine containing urobilinogen at a level of 5 EU/dl.
(EU refers to an Ehrlich's unit)

The test pieces for inspection obtained as described above were immersed in the solutions to be tested (1)–(3), immediately after immersion, removed and allowed to stand for 60 seconds, and their colors were observed.

The following results were obtained:

EXAMPLE C-1

Those described in Examples A-2 and A-4 were used as compositions for test reagent layers and compositions for forming tone layers, and a test device shown in FIG. 7 (without any highly water-absorptive portion) was produced onto a white polystyrene sheet having a width of 8 mm, a length of 90 mm and a thickness of 300 μm as in Example A-2.

EXAMPLE C-2

A test device shown in FIG. 7 was produced as in Example C-1 except that those described in Examples A-2 and B-2 were used as compositions for test reagent layers and compositions for forming tone layers.

EXAMPLE C-3

A test device shown in FIG. 8 was produced as Example C-1 except that the compositions for test reagent layers and the compositions for forming tone layers described in Example A-5 were further used.

EXAMPLE D

Test devices for body fluids having at least one highly water-absorptive portion 4 which are omitted in Examples A-1 through A-5, B-1 and B-2, and C-1 through C-3 were produced. An example of a process for producing the highly water-absorptive portion 4 is described hereinafter.

Production of Highly Water-Absorptive Portions

The following highly water-absorptive composition was finely dispersed in a homomixer, and the highly water-absorptive portions 4a and 4b were screen printed at specific positions. A screen plate used was of 150 mesh, and the sum of the thickness of a resist and a screen gauze was 88 μm.

| Highly water-absorptive composition: | |
| --- | --- |
| Highly water-absorptive resin (manufactured by Sumitomo Kagaku, Japan; Sumika Gel SP-520) | 150 parts by wt. |
| Adhesive (manufactured by Teikoku Ink, Japan; Sericol 13-002 Medium) | 280 parts by wt. |
| Solvent (manufactured by Teikoku Ink, Japan; Sericol 13-002 Solvent) | 70 parts by wt. |

The resulting printed matter was dried for one hour at 60° C. to obtain highly water-absorptive portions.

When the highly water-absorptive portions were provided, the following effect can be obtained. When the test device was immersed in the solution to be tested and then picked up, the solution to be tested which flowed down in a state deposited on the substrate was absorbed by the highly water-absorptive portions. In the case of the shape shown in FIG. 2, the highly water-absorptive portions were in contact with the reagent layer, and therefore the portions of the reagent layer near the highly water-absorptive portions exhibited a slight deficiency of the solution to be tested. Further, in the case of the shape shown in FIG. 6, the upper and lower ends of the reagent layer and the edge portions of the left and right tone layers which were in contact with the highly water-absorptive portions exhibited a slight deficiency of the solution to be tested.

EFFECTS OF THE INVENTION

In the device for testing body fluids according to the present invention, the surface state, surface tension and physical shape of the test reagent layer approximate to those of the tone layer for criterion, wetting of each layer's surface with the solution to be tested is rendered uniform, and the test device of the present invention is so designed that comparison of the hues of the colors can be carried out by their wet colors. Accordingly, the content of the test-objective material in the solution to be tested can be determined with extreme accuracy.

Further, the device for testing body fluids according to the present invention is extremely useful in the detection and treatment of diseases because anyone can easily and quickly judge whether the concentration of the material to be tested in the solution to be tested is within the normal range or not, for example, simply by immersing the test device in the solution to be tested, and because anyone can judge whether close examination in hospitals and test facilities is necessary or not on the basis of such a judgment.

INDUSTRIAL APPLICABILITY

The devices for testing body fluids according to the present invention can accurately and quickly detect test-objective ingredients such as glucose, protein, occult blood, urobilinogen in the body fluids and their pH, and therefore they can be widely utilized as devices for testing body fluids used in hospitals and test facilities.

We claim:

1. A device for testing aqueous body fluids comprising:
   (a) a test reagent layer formed on a substrate and containing a test reagent, a tone of which changes according to a content of test-objective material in an aqueous solution to be tested; and
   (b) a tone layer for criterion formed on the substrate and having a color formed by a coloring agent, said tone layer being compared to a hue of a resulting color or said test reagent layer, said tone layer comprising the coloring agent, a binder, and a water-absorptive powder;
   both said test reagent layer and said tone layer having a property of absorbing the aqueous solution to be tested, and a capacity of the test reagent layer to absorb the aqueous solution to be tested and a capacity of the tone layer to absorb the aqueous solution to be tested are substantially similar;
   wherein the hue of the resulting color of said test reagent layer and the hue of said tone layer are color-compared in their wet state.

2. The device for testing aqueous body fluids according to claim 1, wherein absorption quantities of the aqueous solution to be tested which can be absorbed by the test reagent layer and the tone layer are from 50 to 500% of the respective weights of said layers on a dry basis.

3. The device for testing aqueous body fluids according to claim 2 wherein the absorption quantities are from 100 to 300%.

4. The device for testing aqueous body fluids according to claim 1, wherein said binder comprises a hydrophilic resin, a natural polymeric material or a mixture thereof.

5. The device for testing aqueous body fluids according to claim 1, further comprising a highly water-absorptive portion provided on the substrate.

6. The device for testing aqueous body fluids according to claim 1, wherein the test reagent layer comprises at least one of (a) a composition for glucose detection, (b) a composition for protein detection, and (c) a composition for pH determination.

7. The device for testing aqueous body fluids according to claim 1, wherein the test reagent layer comprises a composition for urobilinogen detection.

8. The device for testing aqueous body fluids according to claim 1, wherein the test reagent layer comprises a composition for urobilinogen detection.

9. The device for testing aqueous body fluids according to claim 1, wherein the test reagent layer and the tone layer are formed with an intervening gap therebetween.

10. The device for testing aqueous body fluids according to claim 9, wherein the gap between the test reagent layer and the tone layer is from 0.2 to 2 mm.

11. A device for testing aqueous body fluids comprising:
   (a) a test reagent layer formed on a substrate and containing a test reagent, a tone of which changes according to a content of test-objective material in an aqueous solution to be tested; and
   (b) a tone layer for criterion formed on the substrate and having a color formed by a coloring agent, said tone layer being compared to a hue of a resulting color of said test reagent layer, said tone layer comprising the coloring agent, a binder, and a water-absorptive powder, wherein a weight ratio of the water-absorptive powder to the binder is from 100:3 to 100:30;
   both said test reagent layer and said tone layer having a property of absorbing the aqueous solution to be tested, and a capacity of the tone layer to absorb the aqueous solution to be tested being less than a capacity of the test reagent layer to absorb the aqueous solution to be tested;
   wherein the hue of the resulting color of said test reagent layer and the hue of said tone layer are color-compared in their wet state.

12. The device for testing aqueous body fluids according to claim 11, wherein the weight ratio of the water-absorptive powder to the binder is from 100:5 to 100:20.

13. A device for testing aqueous body fluids comprising:
   (a) a test reagent layer formed on a substrate and containing a test reagent, a tone of which changes according to a content of test-objective material in an aqueous solution to be tested; and
   (b) a tone layer for criterion formed on the substrate and having a color formed by a coloring agent, said tone layer being compared to a hue of a resulting color of said test reagent layer, said tone layer comprising the coloring agent, a binder, and a water-absorptive powder selected from the group consisting of inorganic powders, cellulose powders, ion exchange resin powders and mixtures thereof;
   both said test reagent layer and said tone layer having a property of absorbing the aqueous solution to be tested, and a capacity of the test reagent layer to absorb to aqueous solution to be tested and a capacity of the tone layer to absorb the aqueous solution to be tested are substantially similar;
   wherein the hue of the resulting color of said test reagent layer and the hue of said tone layer are color-compared in their wet state.

14. A device for testing aqueous body fluids comprising:
   (a) a test reagent layer formed on a substrate and comprising a test reagent and a wetting agent, a tone of said test reagent layer changes according to a content of test-objective material in an aqueous solution to be tested; and
   (b) a tone layer for criterion formed on the substrate and having a color formed by a coloring agent, said tone layer being compared to a hue of a resulting color of said test reagent layer, said tone layer comprising the coloring agent, a binder, and a water-absorptive powder;
   both said test reagent layer and said tone layer having a property of absorbing the aqueous solution to be tested, and a capacity of the test reagent layer to absorb the aqueous solution to be tested and a capacity of the tone layer to absorb the aqueous solution to be tested are substantially similar;
   wherein the hue of the resulting color of said test reagent layer and the hue of said tone layer are color-compared in their wet state.

* * * * *